United States Patent [19]

Nelson et al.

[11] Patent Number: 4,797,550
[45] Date of Patent: Jan. 10, 1989

[54] FIBER OPTIC DETECTOR FOR FLOTATION CELL PROCESSING

[75] Inventors: Michael G. Nelson; Hayward B. Oblad, both of Bethel Park, Pa.

[73] Assignee: Consolidation Coal Company, Pittsburgh, Pa.

[21] Appl. No.: 117,263

[22] Filed: Nov. 6, 1987

[51] Int. Cl.$^4$ ............................ H01J 5/16; H01J 40/14
[52] U.S. Cl. ..................................... 250/227; 250/574; 356/442
[58] Field of Search ................. 250/227, 574; 356/441, 356/442; 366/127

[56] References Cited

U.S. PATENT DOCUMENTS

| | | | |
|---|---|---|---|
| 3,575,383 | 4/1971 | Coleman | 366/127 |
| 3,960,726 | 6/1976 | Peterson | 210/77 |
| 4,040,954 | 8/1977 | Chandler | 210/42 R |
| 4,240,747 | 12/1980 | Harmer | 250/227 |
| 4,529,306 | 7/1985 | Kilham et al. | 250/574 |
| 4,576,723 | 3/1986 | Eisenlauer et al. | 210/709 |
| 4,672,200 | 6/1987 | Claypool et al. | 250/227 |
| 4,675,116 | 6/1987 | Hoyland | 210/709 |
| 4,697,605 | 10/1987 | Yung | 366/127 |
| 4,707,272 | 11/1987 | Kistler | 210/709 |
| 4,711,126 | 12/1987 | Houpt et al. | 250/227 |

FOREIGN PATENT DOCUMENTS

819868 9/1959 United Kingdom.
2182172 5/1987 United Kingdom.

OTHER PUBLICATIONS

Report No. 7623–Photoelectric Concentrator, U.S. Dept of Interior Bureau of Mines; Welsh and Deurbrouck.
"Brinkman Dipping Probe Colorimeters" (12 pages).
"Great Lakes Instruments, Inc. Model 223 Ultrasonic Cleaners" (4 pages).

Primary Examiner—David C. Nelms
Assistant Examiner—William L. Oen
Attorney, Agent, or Firm—Alan N. McCartney

[57] ABSTRACT

An apparatus for determining the reflectivity of the tailings from a coal flotation cell to optimize the cell operation. A bifurcated fiber optic cable has ends connected to a light source and a photoconductor, with a scanner end of the cable being submersed in a coal slurry. Light transmitted to the scanner end of the cable is backscattered to the photoconductor to function as a detector to determine the coal content of the tailings and through a process controller, frother and collector addition to the cell is monitored. An ultrasonic energy vibration is periodically transmitted to the scanner end of the cable to remove deposits thereon to optimize detector operation.

5 Claims, 2 Drawing Sheets

FIBER OPTIC DETECTOR FOR FLOTATION CELL PROCESSING

BACKGROUND OF THE INVENTION

1. Field of the Invention

This invention relates to a fiber optic detector for measuring the relative coal to ash forming impurities content in the tailings of a froth flotation process to monitor the frother addition rate to optimize the coal removal in the flotation cell.

2. Summary of the Prior Art

Various methods and apparatus have been employed to control the operating parameters of flotation cells including the addition of frother additives to the cells to optimize the removal of coal in the cell. In this process, impurities such as ash forming minerals which are the unwanted impurities are separated from the combustible materials (coal). One such device is illustrated in U.S. Pat. No. 4,552,651 which discloses a device for measuring the pulp density in the cell to control cell operation. Another conventional method of controlling cell operation is through the visual observation of the hue of gray in the tailings from the cell. A light gray color will indicate a high impurities content and a darker gray will be indicative of a high coal content in the tailings. This visual inspection by the operator and subsequent manual manipulation of the addition of frother to the cell to optimize coal removal is subject to the obvious disadvantage of inconsistency of control and human error.

Other devices such as nuclear densitometers, coriolis effect mass flow detectors, magnetic flowmeters, dual bubbler tube densitometers and X-ray diffraction equipment have been used to monitor the flotation process, however, these devices are complicated and expensive and do not provide a simple physical reading of the coal content in the tailings from the cell to monitor cell operation.

It is, therefore, desirable to obtain a method and apparatus for automatically measuring the flotation tailings for coal content to control the frother addition rate to the flotation cell to optimize coal removal from the cell.

SUMMARY OF THE INVENTION

In the commonly owned copending U.S. Pat. application Ser. No. 117,264, filed Nov. 6, 1987 there is illustrated a method and apparatus to measure the physical change in the light reflected from the tailings of a coal removal froth flotation cell to control the frother addition rate to the cell to optimize coal removal from the cell. The invention of the copending application provides a photoelectric detector including a light source and light sensor submerged in the tailings from a froth flotation cell which detects the light reflected from the tailings to monitor the addition of frother to the cell to optimize coal removal.

It is the object of this invention to provide a detector by submersing the scanning end of a fiber optic cable in the tailings with the photoconductor and light source exterior of the cell to monitor the activity of the flotation cell.

DESCRIPTION OF THE PREFERRED EMBODIMENT

In the froth flotation process for removal of fine coal from impurities, a frother additive is mixed with the coal in a flotation cell and the slurry is agitated so that bubbles adhere to the coal and the coal rises to the surface of the cell and is removed. The ash forming impurities travel through the cell and are removed from the opposite end and may be further processed. Often times a collector, such as fuel oil, is added to the feed slurry to enhance the attachment of the bubbles to the coal.

An example of such a flotation process is illustrated in commonly owned U.S. Pat. No. 4,552,651 and the disclosure therein is incorporated herein by reference.

Figure 1:
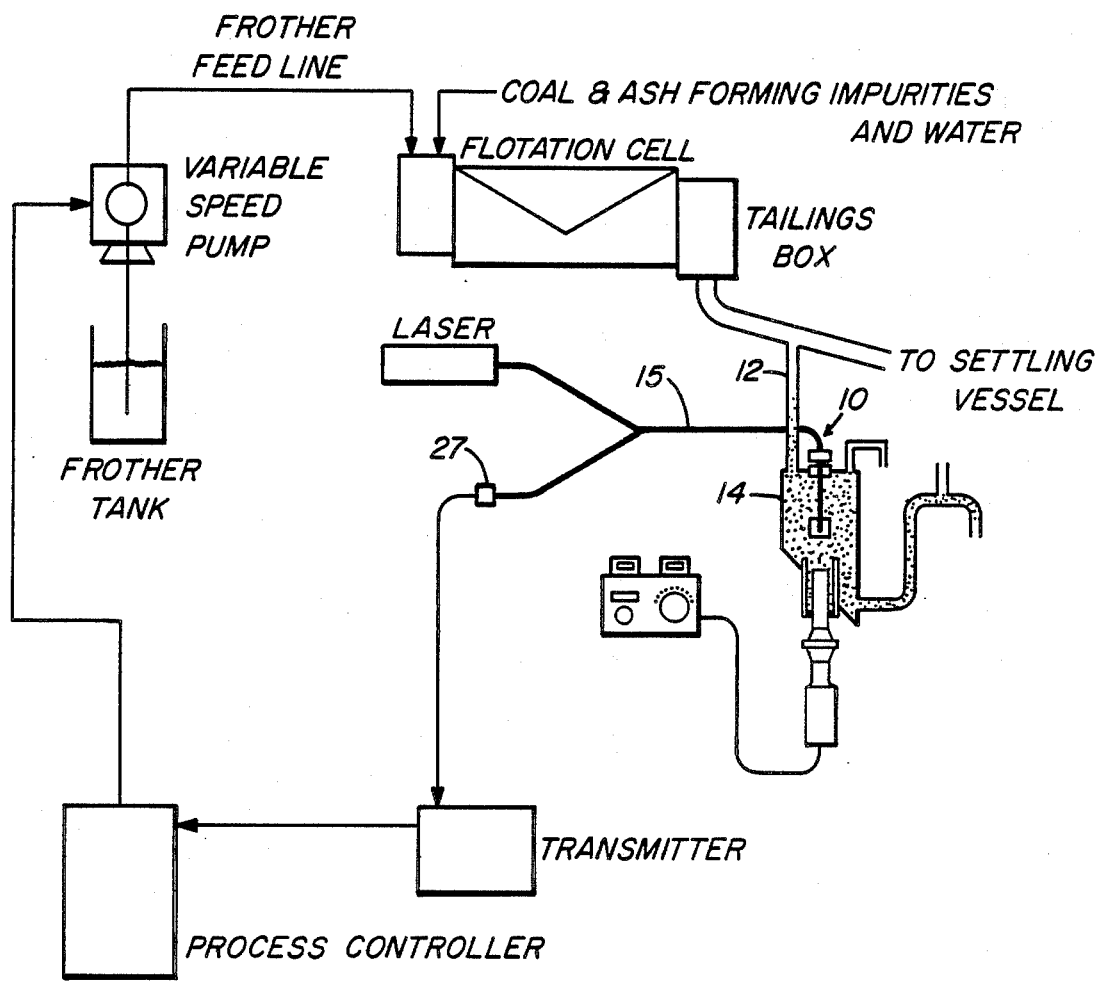
FIG. 1 is a schematic representation of the flotation cell process and the novel method and apparatus for controlling the addition of additives such as frother to the cell to optimize the coal/ash forming impurities separation in the cell.

Attention is directed to FIG. 1 which schematically illustrates the flotation cell which receives the coal and ash forming impurities and water through a feed box. Also added to the feed box is a frother. Aeration of the mix in the cell causes the coal to separate by adhering to the bubbles and the coal is removed from the surface of the cell. The flotation tailings pass through the cell to the tailings box and are removed to a settling vessel for further processing and disposal.

In this process of separating the coal from the ash forming impurities, the degree of the coal separation can be detected in the tailings. If the tailings are a black color, coal is present in large amounts (coal absorbs light), versus the light gray color of the tailings high in clay content and low in coal amounts. Therefore, it is desirable to obtain an automatic reading of the hue of the tailings to determine the coal/ash forming impurities content of the tailings to indicate that an optimum amount of coal has been removed in the flotation cell. A detector of the change in the hue of gray in the tailings will cause a process controller to signal the variable speed frother supply pump in the line between the frother tank and feed box to supply more or less frother to optimize coal removal in the flotation cell. This signal may also be used to regulate the flow of the fuel oil or other collector to the feed slurry.

Figure 2:
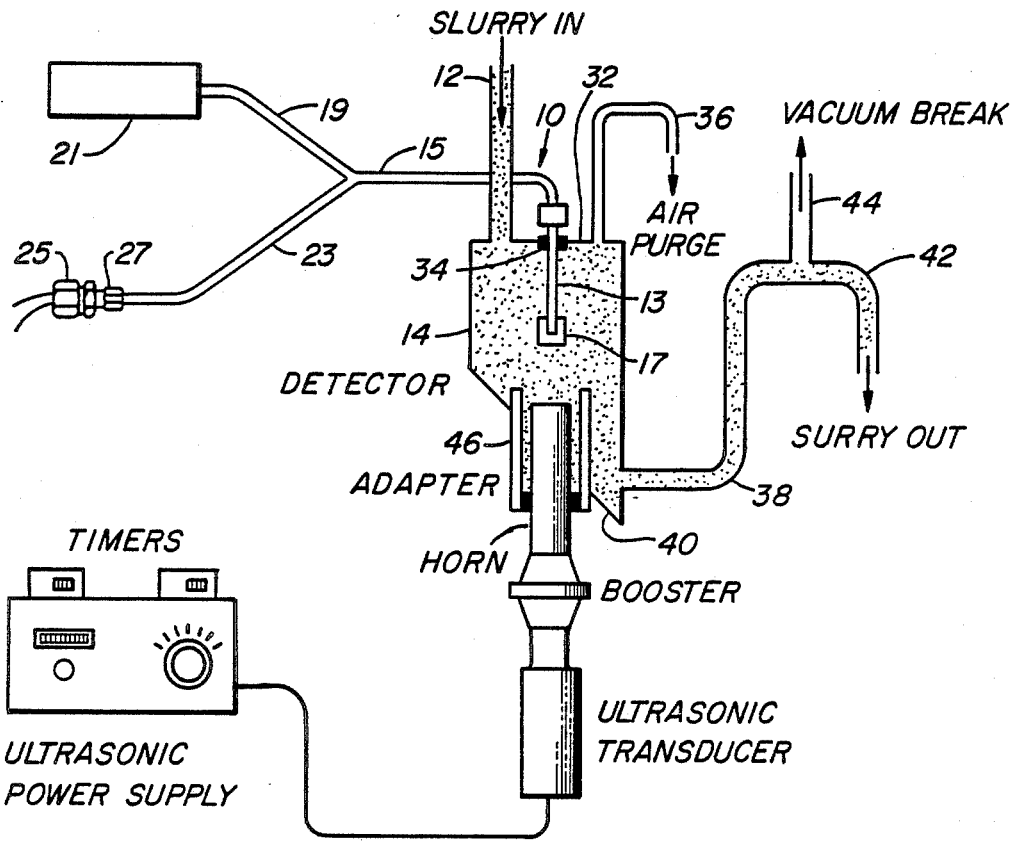
FIG. 2 is a plan view of the novel apparatus for detecting the coal content in the tailings from the flotation cell and illustrating the fiber optic detector.

The above described system of controlling the flotation cell process is accomplished by placing a photoelectric detector 10 in a canister 14 in a bypass line 12 from the line out of the tailings box. As illustrated in FIGS. 1 and 2, the detector 10 comprises a randomized bundle of filaments in a fiber cable 15 having a scanner end 13 carried in a transparent sapphire cap 17 positioned in the canister 14. The fiber optic cable is bifurcated with light sending filaments 19 being connected to a laser light source 21 and the light receiving filaments 23 being connected to a photoelectric sensor 25 in tube fittings 27. The light source 19 is a laser but could be light emitting diodes (LED's) or similar source of constant light. The sensor is a cadmium/sulfide or cadmium selenide photoconductor.

In operation, the light emitted from the laser is passed through filaments 19 out cap 17 and is backscattered from the coal/ash forming impurities slurry to filaments 23 and passed to the photoconductor 25 coupled to a transmitter, see FIG. 1.

As the coal content of the tailings increases, the coal will absorb the light and as the coal content decreases, the hue of gray of the tailings lightens, reflecting more light. This variation in coal content will change the amount of backscattered light sensed by the photoconductor. The change in the resistance in the photoconductor causes the voltage of the constant current output transmitter to change, which voltage is passed to the process controller (see FIG. 1) that controls the variable speed pump and thus the addition of frother and/or collector to the flotation cell Basically, since the resistance of the photosensor is related to the reflectivity of the coal slurry in the tailings, and the reflectivity of the slurry depends on the coal content, then the resistance of the sensor can be correlated to the coal content to monitor coal recovery in the flotation cell.

Referring to FIG. 2, the cable 12 is secured in the upper end 32 of canister 14 by a seal 34 and extends downwardly into the slurry in the canister. An air purge line 36 passes any entrained air out of the canister 14 and the slurry passes out of line 38 connected to the lower sloped surface 40 of the canister. The line 38 extends upwardly to a U-shaped extension 42 above the upper end 32 of the canister to assure that the canister remains full. The rocks and other large particles travel down the slopped surface 40 of the canister, out line 32 up the extension 42 and out for disposal (The vacuum break 44 permits the slurry to pass out the discharge without siphoning out the canister). In this fashion, it can be seen that the configuration of the canister, air purge line 36 and output line 38 permits air to be purged, the canister to remain full and the rocks and slurry to be transferred out of the canister and discharged.

It has been determined that for the above described detector to continuously operate at optimum efficiency, it must emit a constant amount of light which makes the use of a laser or LED's preferable for this application. Additionally, the exposure of the cap 17 to the slurry, coats the cap over a period of time decreasing the accuracy of the sensor. It has been determined that the vibration caused by periodic short bursts of ultrasonic energy will remove any deposits on the cap 17.

To this end (see FIGS. 1 and 2), an ultrasonic transducer is coupled through a booster to a horn passing through a seal 46 in the sloped bottom surface 40 of canister 14. An ultrasonic power supply controlled by timers will periodically energize the ransducer to activate the horn to vibrate the slurry and remove any surface coating on the sapphire cap 17 affecting operation of the detector.

With the use of a hardened surface cap, such as sapphire cap 17 in the slurry, the glass fibers in the sensing end of cable 12 are protected from erosion and discoloration caused by the impurities in the slurry, while still maintaining the required sensitivity to the scanner end 12 of the detector 10. Further, with the light emitter and sensor being isolated from the slurry, the entire detector is simpler in construction and will have a longer useful life.

Figure 3:
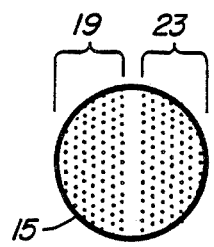
FIG. 3 is a sectional view of one type of fiber optic cable.
Figure 4:
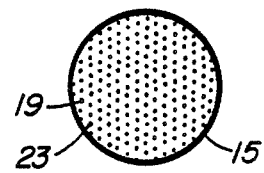
FIG. 4 is a sectional view of the preferred type of fiber optic cable to be utilized with this invention.

Attention is now directed to FIGS. 3 and 4 which illustrate different arrangements of glass filaments in a fiber optic cable. In FIG. 3, the filaments are uniform or not randomized in their position. In FIG. 4, the filaments are randomly spaced. When using a filament arrangement as in FIG. 3 for this invention, the light sending filaments 19 are spaced from the receiving filaments 23 thus decreasing the sensitivity of the detector. When a randomized cable, as illustrated in FIG. 4 is used, the sending and receiving filaments are closely spaced and randomly distributed in the filament bundle, increasing the sensitivity of the detector 10 and permitting the light source to be smaller and less powerful and lighter for the sensitivity desired.

It can thus be seen from the described apparatus, that the physical properties of coal content of the flotation cell tailings can be detected and utilized to control the flotation cell to optimize coal removal from the cell.

I claim:

1. An apparatus for automatically monitoring the operatsion of a froth flotation cell for extracting coal from a coal slurry, the cell having an outlet from a tailings box; comprising
   (a) a canister for receiving tailings from a bypass line out of the tailings box;
   (b) a fiber optic cable having randomized filaments terminating in a scanner end portion adapted to be inserted into said canister;
   (c) said cable being bifurcated at the opposed end spaced from the slurry and having randomized filaments contacting a light source and randomized filaments contacting a light receiving photoelectric sensor, said light source filaments transmitting light to said scanning end portion, and said light receiving filaments transmitting backscattered light from the tailings to said photoelectric sensor to sense the hue of the color of the tailings to monitor the operation of the flotation cell.

2. The apparatus of claim 1 wherein said scanner end portion contains a hardened cap to protect said scanner end portion from any debris in the slurry.

3. The apparatus of claim 2 wherein said cap is a sapphire material.

4. The apparatus of claim 1 including means to vibrate the slurry to remove debris from said scanner end portion.

5. The apparatus of claim 4 wherein said vibrating means is a source of ultrasonic energy.

* * * * *